US00PP10002P

United States Patent [19]

Meilland

[11] Patent Number: Plant 10,002

[45] Date of Patent: Aug. 19, 1997

[54] MINIATURE ROSE PLANT NAMED 'MEILMERA'

[75] Inventor: Alain A. Meilland, Antibes, France

[73] Assignee: The Conard-Pyle Company, West Grove, Pa.

[21] Appl. No.: 682,311

[22] Filed: Jul. 17, 1996

[30] Foreign Application Priority Data

May 2, 1996 [FR] France ..... 14897

[51] Int. Cl.[6] ..... A01H 5/00

[52] U.S. Cl. ..... Plt./8.1

[58] Field of Search ..... Plt./7.1, 8.1, 8.2

*Primary Examiner*—Howard J. Locker

*Attorney, Agent, or Firm*—Burns, Doane, Swecker & Mathis, L.L.P.

[57] ABSTRACT

A new and distinct variety of rose plant of the miniature class is provided which abundantly forms attractive generally white very double blossoms that commonly are arranged in clusters. The plant exhibits an erect growth habit and forms medium-green glossy vegetation. The blossoms possess no fragrance. The plant is well adapted for growing as attractive ornamentation in pots, and grows well on its own roots. The blossoms are very long lasting.

1 Drawing Sheet

SUMMARY OF THE INVENTION

The new variety of miniature rose plant was created by artificial pollination wherein two parents were crossed which previously had been studied in the hope that they would contribute the desired characteristics. The female parent (i.e., the seed parent) was the product of the pollination of the 'Meiringa' variety U.S. Pat. No. P.P. 3,804) and the 'Scheewittchen' variety (non-patented in the United States). The 'Meiringa' variety sometimes is known as the 'Carte Blanche' variety. The male parent (i.e., the pollen parent) of the new variety was the product of the pollination of the 'Meizogrel' variety (U.S. Pat. No. P.P. 7,276 ) and the 'Meilarco' variety (U.S. Pat. No. P.P. 6,170). The 'Meizogrel' variety is marketed under the WHITE MINI-WONDER trademark, and the 'Meilarco' variety is marketed under the LADY SUNBLAZE trademark. The parentage of the new variety can be summarized as follows:

('Meirigna'×'Schneewittchen')×('Meizogrel'×'Meilarco').

The seeds resulting from the above pollination were sown and small plants were obtained which were physically and biologically different from each other. Selective study resulted in the identification of a single plant of the new variety.

It was found that the new variety of miniature rose plant of the present invention possesses the following combination of characteristics:

(a) forms in abundance attractive generally white very double very long lasting blossoms that commonly are arranged in clusters,
(b) forms medium-green glossy foliage,
(c) exhibits an erect growth habit,
(d) is well adapted for growing in a pot as ornamentation, and
(e) grows well on its own roots.

The blossom petals tend to be shorter in height at the center of such blossoms (as illustrated).

The new variety well meets the needs of the horticultural industry. It is particularly well-suited for use as attractive ornamentation when grown in a pot.

The new variety has been found to undergo asexual propagation in France by a number of routes, including budding, grafting, cuttage, etc. Asexual propagation by the above-mentioned methods as performed in France has shown that the characteristics of the new variety are strictly transmissible from one generation to another.

The new variety has been named the 'Meilmera' variety, and is marketed under the BRIDAL SUNBLAZE trademark.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety described herein were one year of age and were observed during April while growing on their own roots in greenhouses at LeCannet des Maures, Var, france.

FIG. 1 — illustrates a specimen of a young shoot;

FIG. 2 — illustrates specimens of two floral buds before the opening of the sepals;

FIG. 3 — illustrates specimens of two floral buds at the opening of the sepals;

FIG. 4 — illustrates specimens of two floral buds at the opening of the petals;

FIG. 5 — illustrates specimens of two flowers during the course of opening;

FIG. 6 — illustrates a specimen of an open flower — plan view — obverse;

FIG. 7 — illustrates a specimen of an open flower — plan view — reverse;

FIG. 8 — illustrates a specimen of a fully open flower — plan view — obverse;

FIG. 9 — illustrates a specimen of a fully open flower — plan view — reverse;

FIG. 10 — illustrates a specimen of a floral receptacle showing the arrangement of the stamens and the pistils;

FIG. 11 — illustrates a specimen of a floral receptacle showing the arrangement of the pistils (stamens removed);

FIG. 12 — illustrates a specimen of a flowering stem;

FIG. 13 — illustrates a specimen of a main branch;

FIG. 14 — illustrates specimens of leaves with three leaflets with the upper surface being shown at the top and the under surface being shown at the bottom;

FIG. 15 — illustrates specimens of leaves with five leaflets with the upper surface being shown at the left and the under surface being shown at the right; and FIG. 16 — illustrates specimens of leaves with seven leaflets with the upper surface being shown at the top and the under surface being shown at the bottom.

DETAILED DESCRIPTION

Figures 1, 2, 3, 4, 5, 6, 7, 8, 9, 10, 11, 12, 13, 14, 15, 16:
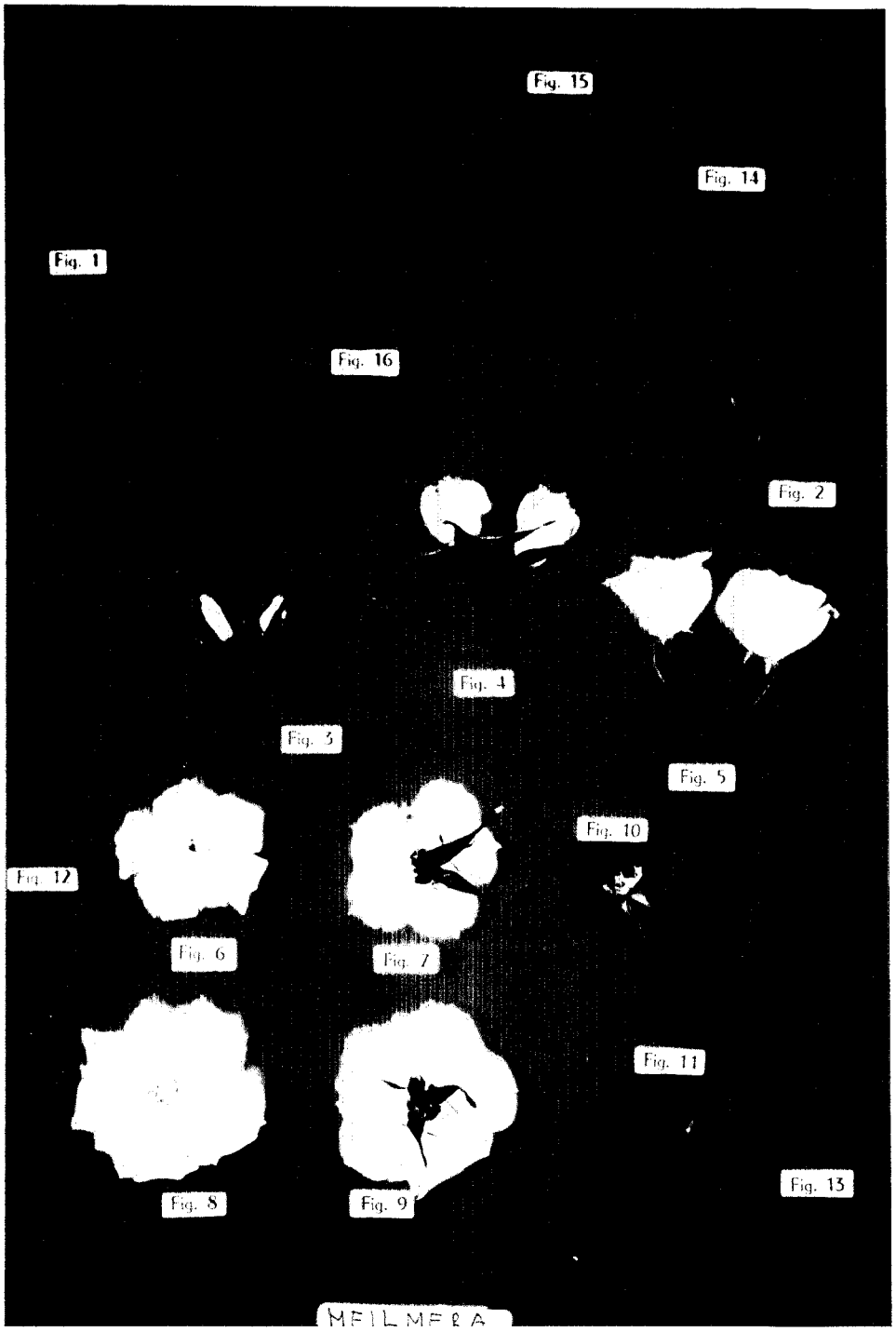

The chart used in the identification of the colors is that of The Royal Horticultural Society (R.H.S. Colour Chart). The terminology which precedes reference to the chart has been added to indicate the corresponding colors in more common terms. The description is based on one year-old specimens of the new variety which were observed during October while growing on their own roots in greenhouses at LeCannet des Maures, Var, France.

Class: Miniature.

Plant:

*Height.*—Approximately 45 cm. on average at the end of the growing season.

*Habit.*—Erect.

Branches:

*Color.*—Young stems: near Lettuce Green, Yellow Green Group 144A and more or less suffused with reddish brown. Adult wood: Yellow-Green Group 144A.

*Thorns.*—Size: medium. Quantity: numerous. Color: pinkish to Havana brown.

Leaves:

*Petioles.*—upper surface: striped, reddish on young foliage and medium green on mature foliage with glandular edges. Under surface: light green and bear many small thorns.

*Stipules.*—Adnate, pectinate, and rather narrow and linear.

*Leaflets.*—Number: 3, 5, and 7 (most often). Shape: lanceolate. Serration: simple and regular (as illustrated). Texture: consistent. General appearance: dense and glossy medium green foliage. Color (young foliage): Upper surface: Lettuce Green, Yellow-Green Group 144A and lightly edged with reddish brown. Under surface: Lettuce Green, Yellow-Green Group 144A and lighly edged with reddish brown. Color (adult foliage): Upper surface: dark green, Green Group 137A. Under surface: lighter green, near Green Group 137C.

Inflorescence:

*Number of flowers.*—Approximately 2 to 5 per stem and commonly in clusters.

*Peduncle.*—Medium green, rarely possesses an acicule, and its length commonly is approximately 6 cm. on average.

*Sepals.*—Upper surface: tomentose and greenish in coloration. Under surface: light green with few extensions (as illustrated).

*Bud.*—Shape: conical form. Length: approximately 1.5 cm. on average. Size: medium for this class. Color upon opening: Upper surface: light green, near Yellow-Green Group 145C. Under surface: light green, near Yellow-Green Group 145C.

*Flower.*—Form: cupped, with very double petals. Diameter: approximately 6 cm. on average. Color (when opening begins): Upper surface: near Yellow Group 2D with light green coloration at the base. Under surface: near Yellow Group 2D with light green coloration at the base. Color (when blooming): Upper surface: the external petals are near White Group 155A and lightly tinted with yellowish coloration at the base, and the internal petals are near White Group 155A at the margins and near Yellow Group 5C towards the middle. Under surface: the external petals are near White Group 15A and lightly tinted with yellowish coloration at the base, and the internal petals are near White Group 15A at the margins and near Yellow Group 5C towards the middle. Color (at end of blooming): Upper surface: the external petals are near White Group 155A, and the internal petals are White Group 155A and lightly tinted with Yellow Group 2C at the base. Under surface: the external petals are near White Group 155A, and the internal petals are White Group 155A and lightly tinted with Yellow Group 2C at the base. Fragrance: none. Lasting quality: very long when grown indoors with blossoms commonly lasting up to two weeks or more. Petal number: approximately 75 on average. Petal form: lanceolate with reflexed edges and obtuse base with the petals tending to be shorter in height at the center. Petal drop: good with the petals tending to detach cleanly when the blossoms are fully mature. Anthers: normal and ochre in coloration. Stamen number: approximately 17 on average. Filaments: normal and greenish in coloration. Pistil number: approximately 20 on average. Sigmas: yellowish in coloration. Styles: greenish in coloration. Receptacle: medium green, smooth, and in longitudinal section in the shape of a funnel.

Development:

*Vegetation.*—Strong.

*Blooming.*—Very abundant.

*Resistance to diseases.*—Good.

I claim:

1. A new and distinct variety of miniature rose plant characterized by the following combination of characeristics:

(a) forms in abundance attractive generally white very double very long lasting blossoms that commonly are arranged in clusters,
(b) forms medium-green glossy foliage,
(c) exhibits an erect growth habit,
(d) is well adapted for growing in a pot as ornamentation, and
(e) grows well on its own roots;

substantially as herein shown and described.

* * * * *

MEILMERA